(12) United States Patent
Haenke

(10) Patent No.: US 7,435,705 B2
(45) Date of Patent: *Oct. 14, 2008

(54) ENVIRONMENTALLY SAFE ANTI-FUNGAL COMPOSITION AND METHODS OF USING SAME

(76) Inventor: Jodi Haenke, 3962 Crayrich Cir., Orlando, FL (US) 32839

( * ) Notice: Subject to any disclaimer, the term of this patent is extended or adjusted under 35 U.S.C. 154(b) by 362 days.

This patent is subject to a terminal disclaimer.

(21) Appl. No.: 11/032,980

(22) Filed: Jan. 11, 2005

(65) Prior Publication Data

US 2005/0119335 A1 Jun. 2, 2005

Related U.S. Application Data

(63) Continuation-in-part of application No. 10/410,515, filed on Apr. 8, 2003, now Pat. No. 6,841,570.

(60) Provisional application No. 60/370,650, filed on Apr. 8, 2002.

(51) Int. Cl.
*A01N 43/16* (2006.01)
*A01N 59/00* (2006.01)

(52) U.S. Cl. .................... 504/150; 514/456

(58) Field of Classification Search .......... 514/456, 514/724; 424/405; 504/150
See application file for complete search history.

(56) References Cited

U.S. PATENT DOCUMENTS 5,403,587 A * 4/1995 McCue et al. .............. 424/736
6,254,897 B1  7/2001 Shao
2003/0156974 A1 * 8/2003 Haas et al. .................. 422/28

FOREIGN PATENT DOCUMENTS

| JP | 09118629 A | * | 5/1997 |
| WO | WO 2003 097727 | | 11/2003 |
| WO | WO 2003 104561 | | 12/2003 |
| WO | WO 2004 089357 | | 10/2004 |

OTHER PUBLICATIONS

Thomas R. Hoffman, Selecting Preservative Treat Woos with Special Emphasis on Landscape Timbers, 1995, Regents of the University of Minnesota, pp. 1-17.*

News Release, Catnip Repels Mosquitoes More Effectively Than Deet, American Chemical Society, Aug. 28, 2001.*

Extraction Methods and Bioautography for Medicinal Plant Antimicrobial Activity, A. Nostro, M. P. Germano, V. D'Angelo, A. Marino and M. a. Cannate, Letters in Applied Microbiology. vol. 30, issue 5, p. 379, May 2000.

Bourrel, C., Perineau, F. Michael, G., Bessiere, J.M. (1993) Catnip (*Nepeta cataria* L.) essential oil: analysis of chemical consitutents, bacteriostatic and fungistatic properties, Journal of Essential Oil Research 5, 159, 167.

* cited by examiner

*Primary Examiner*—Johann Richter
*Assistant Examiner*—Andriae M Holt
(74) *Attorney, Agent, or Firm*—Timothy H. Van Dyke; Beusse Wolter Sanks Mora & Maire

(57) ABSTRACT

Disclosed herein or novel, environmentally friendly compositions and methods for treating or preventing fungal growth, such as molds and mildew, on surfaces and in objects. Specifically exemplified herein are compositions containing nepetalactone, and methods of using same.

14 Claims, No Drawings ously wetted materials that contain cellulose, for example, including interior wall paneling, such as gypsumboard, and other materials used in residential and commercial buildings including cardboard, ceiling tiles, cellulose insulation, wood, etc.
ENVIRONMENTALLY SAFE ANTI-FUNGAL COMPOSITION AND METHODS OF USING SAME

CROSS-REFERENCE TO RELATED APPLICATIONS

This application is a continuation in part of U.S. patent application Ser. No. 10/410,515, filed Apr. 8, 2003, now U.S. Pat. No. 6,841,570 which is related to and claims priority to U.S. Provisional Patent Application No. 60/370,650, filed Apr. 8, 2002. This application claims priority to the foregoing applications and incorporates by reference their disclosures in their entirety.

BACKGROUND OF THE INVENTION

Growth of fungi, such as certain types of black or gray molds in residential and commercial buildings, can produce significant health hazards to human occupants of such buildings. For example, the black molds known as *Stachybotrys* and *Memnoniella* are types that are known to produce mycotoxins which are hazardous to human health when exposure is encountered. These mold types typically occur on repeatedly wetted materials that contain cellulose, for example, including interior wall paneling, such as gypsumboard, and other materials used in residential and commercial buildings including cardboard, ceiling tiles, cellulose insulation, wood, etc.

Fungi, primarily *Aureobasidium pullulans*, are responsible for the mildew growth seen on the exterior painted surfaces of houses, particularly in warm, damp climates. Algae, primarily *Chlorophyta* and *Myxophyceae* also appear on such painted surfaces. Fungi, primarily *Aspergillus niger*, are responsible for the mildew growth seen on hard indoor surfaces, such as bathroom tile and grout. Removal of such algae and fungi from hard surfaces, particularly painted surfaces, is a difficult problem. If the fungi and algae are not completely removed from painted surfaces they could reappear at a rate faster than that at which they were observed growing originally. Detergent compositions, as disclosed in U.S. Pat. Nos. 4,097,395 and 4,164,477, are known for cleaning hard surfaces. These compositions contain a fungicide, detergent and organic acid as well as components that function as degreasants, wetting agents, sequestering agent, penetrants and the like. The detergent compositions are diluted with a bleach just prior to application.

There are several sources of moisture which can accelerate and promote the growth of gray and black molds including the types mentioned above. Water piping extending through plumbing chases and piping extending through voids or spaces in interior walls of residential and commercial buildings can produce minute leaks sufficient to wet adjacent materials and promote the growth of mold. Leakage from the exterior of a building into various parts of the building, which goes undetected, can also wet the surfaces of various materials which will promote the growth of toxic molds. Still further, condensation, from time to time, on the surfaces of plumbing piping, air conditioning ducts, refrigerant conduits and other structures is also a source of moisture which can result in the growth of molds in unseen spaces, such as the interior wall spaces of buildings, among other locations, all of which are a source of mold contamination and exposure to humans.

The growth of mold in interior wall spaces in residential and commercial buildings is particularly difficult to detect and difficult to eradicate by conventional methods. Since the interior wall spaces have been covered with various types of wall paneling, the growth of mold goes undetected and, when detected, is difficult to treat without major renovation of the building. Accordingly, there has been a longstanding need for the development of mold and other pest prevention systems and treatment methods which can eliminate toxic molds, in particular, from various places within a residential or commercial building, including interior wall spaces, plumbing chases, and virtually any portion of a building structural feature which is likely to be exposed to moisture, repeatedly, during the life of the building. It is to these ends that the system and methods of the present invention have been developed. A broad range of organic molecules have been found to have fungicidal and bactericidal properties and are effectively used for plant disease control. However, many of the currently used pesticides pose a high risk to human health and the environment and are not biodegradable. Since the establishment of the Environmental Protection Act in 1972 there has been an increased concern over the use of toxic chemicals for plant disease control and the dangerous residual potential these toxic products represent. The United States Congress disclosed its concerns with those products with the passage of the Food Quality Protection Act in August, 1996 which requires the U.S. EPA to reassess each existing pesticide by 2006. Because of toxicity concerns, to reduce residues on crops, fruits and vegetables, the application of pesticides shortly before harvest must usually be avoided. Additionally, because of concerns regarding the health of workers, entry into fields or greenhouses shortly after pesticide application is usually prohibited.

Therefore, there is a real need to provide more biocompatible fungicides and bactericides which are, by definition, safe in the environment, non-toxic to humans and animals, and which are rapidly biodegradable.

DETAILED DESCRIPTION

Catnip, *Nepeta cataria*, is a member of the mint or Labiatae family. This perennial herb is sometimes known as catnep, catrup, catwort, cataria, or catmint (although there are other plants that also go by these common names). Catnip is indigenous from the eastern Mediterranean region to the eastern Himalayas, but is naturalized over much of North America and is easily grown in most gardens. The generic name *Nepeta* is said to have been derived from the Italian town Nepete, where catnip was once cultivated. For centuries humans have grown catnip for humans, but the herb is best known for its action on cats. Nepetalactone is a terpenoid composed of two isoprene units, with a total of ten carbons. Its chemical structure is similar to that of the valepotriates derived from the herb valerian, which is a mild central nervous system sedative (or stimulant to some persons).

Accordingly, the term "nepetalactone" as used herein refers to, but is not limited to, crude catnip, the oil obtained from *Nepeta cataria*, 5,6,7,7a-tetrahydro-4,7-dimethyl cyclopenta[c]pyran-1-(4aH)-one, and isomers, analogs and derivatives thereof, nepetic acid, nepetalic acid, (4aS,7S,7aR)-nepetalactone, (1R,4aS,7S,7aR)-nepetalactol, cis/trans nepetalactone see U.S. Pat. No. 6,524,605, and nepetalactone-derived compounds whereby nepetalactone is a precursor, intermediate or reagent in forming said nepetalactone-derived compounds. Further, specific substitution of reactive constituents on or emanating from the two rings of nepetalactone may include one or more of the following: a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$-$C_6$ straight or branched chain alkyl, $C_2$-$C_6$ straight or branched chain alkenyl or alkynyl, aryl, aralkyl, heteroaryl, carbocycle, or heterocycle group or moiety, or $CO^2R^7$ where $R^7$ is hydrogen or $C_1$-$C_9$ straight or branched chain alkyl or $C_2$-$C_9$ straight or branched chain alkenyl group or moiety. In addition, nepetalactone-derived compounds may include a pharmaceutically acceptable salt, ester, or solvate thereof. Furthermore, based on the teachings herein, those skilled in the art will appreciate the value of isolating genes responsible for the biosynthesis of nepetalactone. Therefore, nepetalactone may be recombinantly produced utilizing known genetic manipulation and molecular and cell biology techniques. It is intended that nepetalactone as defined above can be used as a termite and other wood-boring insect repellant and insecticide in accord with the teachings herein and in the related U.S. patent application Ser. No. 10/410,515. As used herein, wood-boring insects refers to, but is not limited to, all species of termites, carpenter ants, carpenter bees, and powderpost beetles. Furthermore, nepetalactone may be used to eradicate, reduce or prevent fungal and/or algae growth. The terms fungal, fungus and fungi as used herein are to be interpreted to include algae as well as fungi in the traditional sense.

The subject invention is a further development from the inventor's discovery that nepetalactone, an oil found in *Nepeta cataria* (commonly known as catnip), has a dramatic repellant effect on termites. The inventor has also found that at certain concentrations, nepetalactone is lethal to termites. Inventions related to such discovery were described in U.S. patent application Ser. No. 10/410,515, whose teachings are incorporated herein in their entirety. Through continuous testing of nepetalactone, the inventor has discovered that nepetalactone has a surprising, unexpected anti-fungal ability. Though, others have tenuously discussed that essential plant oils may possess certain anti-fungal abilities, see for example PCT Publication No. 2004/089357, to the inventor's knowledge no one heretofore recognized or appreciated the powerful fungicidal ability of nepetalactone, especially against molds, mildews, and algae found in and around residential and commercial buildings. The inventor has observed strong anti-fungal properties of nepetalactone using compositions containing less than 1 percent, by weight, nepetalactone. In her validation experiments, the inventor has applied an extremely dilute nepetalactone composition (containing at least 99 percent water) to an external building wall covered with a mold. Though the study was not quantitative, the surface treated with nepetalactone was entirely free of any visible mold growth, whereas the control treated surface had no sign of mold reduction.

Therefore, one aspect of the invention pertains to a novel composition comprising nepetalactone and formulated for treatment and prevention of fungal growth. The composition may act as a fungicide or to reduce fungal infestation, or to prevent fungal growth on a surface or in an object, which is broadly defined as "anti-fungal" activity or properties, in the present application.

The present invention provides a system and methods for preventing or eliminating fungi, such as gray or black mold, from various surfaces of a residential and/or commercial building including interior wall spaces, kitchen and bathroom areas and surfaces, plumbing chases and other portions of a building structure which are likely to serve as a place for growth of such mold. In one embodiment, the subject invention may be implemented as an environmentally safe treatment of fungi present on roof shingles or tiles, or as a preventative treatment.

In accordance with one aspect of the present invention, a fungal growth prevention or eradication method is provided which includes the steps of applying a suitable anti-fungal composition to fungal susceptible surfaces, i.e., those which are likely to allow growth of fungi thereon. For example, such surfaces are those present in a moist and/or warm environment, or other environmental conditions which or conducive to fungal growth. In a typical embodiment, application is conducted via delivery of a spray of a predetermined liquid particle size. A method in accordance with the invention may include that of applying the anti-fungal composition to exposed interior surfaces of exterior walls of the building or structure, which may be done prior to installing interior wall panels or coverings at said exterior walls. The method also may include applying an anti-fungal composition, to all plumbing chases and interior walls in rooms which include plumbing piping, such as bathrooms, kitchens, and the like. The treatment method preferably further includes applying the anti-fungal composition to wall column members, or so-called studs, floor plates, the interior surfaces of wallboard or paneling and other structural features which include cellulose or other mold growth promotion materials as part of the composition of the structural member. Still further, the treatment method involves application of the anti-fungal composition to the perimeter of the building flooring, a predetermined distance in from an exterior wall, including treatment of second and third story subflooring and decking, and treatment at or in the vicinity of all roof penetrations of the building. Further still, application comprises applying to sinks, counter tops, walls and appliances in a kitchen, or toilets, sinks, baths and showers, and walls in a bathroom. Moreover, application comprises applying to roof shingles and tiles to treat such infected with fungi such as saprophytic type fungi. The composition of the invention can be applied to the affected surface, or surface prone to fungal growth, using any one of a number of methods, including, but not limited to, spraying, brushing, rolling, pouring, and/or dipping. Preferably, the composition is applied using an applicator such as a garden sprayer, airless paint sprayer, compressor paint sprayer or hand pump sprayer. The composition can also be applied using a sponge or brush.

As used in this disclosure, the term "effective anti-fungal concentration" is defined to indicate a concentration at which nepetalactone works to reduce fungal growth on a surface of or within an object. The longevity of such effect may be extended by means known in the art, including but not limited to: emulsions, encapsulation, microencapsulation; mixing with carriers; mixing with preservatives; and applying into areas and/or devices that have limited exposure to the elements and/or a limited egress for the evaporative loss of nepetalactone.

In one method, nepetalactone is combined with a carrier containing a preservative, and is applied along the outside walls and/or roof of a building structure in need of fungal eradication or fungal reduction.

In another preferred embodiment, nepetalactone is microencapsulated by any of the many methods of microencapsulation known to those skilled in the art of microencapsulation. Preferably, the microencapsulation method is chosen to allow a slow release of nepetalactone. Optionally the microencapsulated nepetalactone is mixed with a carrier, or applied in a liquid suspension, and is preferably uniformly dispersed.

A carrier in the present context is any material with which nepetalactone is formulated to facilitate application to the locus, or storage, transport or handling. A carrier can be a solid or a liquid, including a material which is normally gaseous but which has been compressed to form a liquid. Any of the carriers normally used or known to be usable in formulating insecticidal compositions may be used.

Compositions according to the invention comprise about 0.000001 to 99.9% by weight active ingredient. Preferably, compositions according to the invention comprise about 0.0001 to 10.0% by weight of active ingredient, more preferably, about 0.005 to 5.0%. More preferably, the active ingredient comprises 0.01 to 1%, by weight.

Suitable solid carriers include natural and synthetic clays and silicates, for example natural silicas such as diatomaceous earths; magnesium silicates, for example talcs; magnesium aluminum silicates, for example attapulgites and vermiculites; aluminum silicates, for example kaolinites, montmorillonites and micas; calcium carbonate; calcium sulphate; ammonium sulphate; synthetic hydrated silicon oxides and synthetic calcium or aluminum silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example superphosphates. Cellulose based materials, for example wood, sawdust, agar or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable. Suitable liquid carriers include water; alcohols, including, but not limited to, for example isopropanol, ethanol, methanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone. Mixtures of different liquids are often suitable, for example a mixture of isophorone with a polar organic solvent such as N-methylpyrrolidone, as are mixtures of solid and liquid carriers.

Anti-fungal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surface-active agent. For example, the composition may contain at least two carriers, at least one of which is a surface-active agent. A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfonated castor oil, and sodium alkylaryl sulfonates such as dodecylbenzene sulfonate; and polymers of ethylene oxide and copolymers of ethylene oxide and propylene oxide.

Compositions can, for example, be formulated as wettable powders, dusts, granules, baits, solutions, emulsifiable concentrates, emulsions, suspension concentrates, and aerosols. Compositions can be encapsulated or microencapsulated, preferably to effect slow, controlled release of the active ingredient. Wettable powders preferably contain 0.005, 0.05, 0.5, 1.0, 5.0, 10.0, 15.0, 20.0, 30.0, 40.0, 50.0, or 75% weight of active ingredient and preferably contain in addition to solid inert carrier, 3-10% weight of a dispersing agent and, where necessary, 0-10% weight of stabilizer(s) and/or other additives such as penetrants or stickers.

Dusts are usually formulated as a dust concentrate having a similar composition to that of a wettable powder but without a dispersant, and are diluted in the field with further solid carrier to give a composition usually containing 0.005-10% weight of active ingredient, preferably 0.05 to 5%.

Granules are usually prepared to have a size between 10 and 100 BS mesh (1.676-0.152 mm), and may be manufactured by, for example, agglomeration or impregnation techniques. Generally, granules will comprise about 0.001-75% (preferably 0.05 to 20%) weight active ingredient and 0-10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3-7% by weight of a blend of surfactants, which act as wetting dispersing, suspending and binding agents, and 1-3% by weight of a finely divided carrier, which acts as a resuspending agent.

Wood or timber is impregnated with active ingredient according to well known procedures including pressure treatments such as the Lowery empty cell process and full cell process, vacuum treatments, hot and cold bath treatment, thermal treatment, and cold-soak treatment. Surface treatment of wood or timber is accomplished by well known techniques such as brushing, dipping, infusing, coating, spraying or short-soaking the wood material with active ingredient or appropriate compositions thereof in amounts and in a manner that would be apparent to one skilled in the art.

For instance, wood treatments may be accomplished by two major methods: impregnation of the wood through vacuum and pressure treatments and surface treatments such as painting, coating, spraying or dipping. In an impregnation method, a concentrate may be formulated which comprises about 0.01-65% weight per volume active ingredient, 5-50% solvent and, when necessary, co-solvent, and 0-40% w/v of other additives such as penetrants. For treatment, vacuum is pulled on a vessel containing the wood. The concentrate is then added to the vessel and subsequently pressurized to force concentrate into the wood. The vessel is relieved of pressure and the treated wood then removed. In a surface treatment, the concentrate may be simply painted onto a wood surface by means of brushing or spraying or, preferably, dipping. Solvents used for these types of treatments may include polyethylene glycol, and aromatic solvents, and the like due to their ability to penetrate wood.

Emulsifiable concentrates usually comprise, in addition to a solvent and, when necessary, co-solvent, about 0.01-50% weight per volume active ingredient, 2-50% weight per volume emulsifiers and 0-50% weight per volume of other additives such as stabilizers, penetrants and corrosion inhibitors.

Suspension concentrates are usually compounded so as to obtain a stable, non-sedimenting flowable product and usually comprise about 0.01-75% weight active ingredient, 0.5-15% weight of dispersing agents, 0.1-10% weight of suspending agents such as protective colloids and thixotropic agents, 0-10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water. The suspension may be finely ground crude catnip. Suspendable, finely ground particles of crude catnip may be a cost-effective alternative, as it will avoid costs involved in isolating nepetalactone from crude catnip.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency. Compositions can also comprise other ingredients, for example, further active compounds possessing herbicidal, insecticidal or fungicidal properties, in accordance with the requirement of the locus to be treated and the treatment method.

Other mixtures than the mixtures exemplified above may be used for application on materials such as woods, as emulsifiable concentrates, and as suspension concentrates. Preferred final composition concentrations may range from 0.000001 to 10.0 percent by weight, or more preferably from 0.005 to 5.0 percent by weight, or even more preferably from 0.01 to 1.0 percent by weight, depending on the application.

The method of applying an extract of this invention to prevent or treat infestation of termites comprises applying nepetalactone, conveniently in a composition comprising the nepetalactone of this invention and a carrier as described above, to a locus or area to be treated for the termites, such as soil or timber, already subject to infestation or attack by termites or intended to be protected from infestation by termites. The active ingredient is, of course, applied in an amount sufficient to effect the desired action of combatting termite infestation or eradication, reduction or protection against fungal growth. This dosage is dependent upon many factors, including the carrier employed, the method and conditions of the application, whether the formulation is present at the locus in the form of a film, or as discrete particles or as a bait, the thickness of film or size of particles, the degree of termite infestation, the duration of persistence desired or required, and the like. Proper consideration and resolution of these factors to provide the necessary dosage of the active ingredient at the locus to be protected are within the skill of those versed in the art. In general, however, the effective dosage of the compound of the invention at the locus to be protected is typically about 0.0001 to 10.0% based on the total weight of the composition, preferably, about 0.02% to 5%.

In one embodiment of this invention, the compositions of this invention are used to combat termites in the soil, thereby achieving indirect protection for any wood or wood-based constructions erected on the treated soil or to crops, grassland, forestry (especially young saplings), and other cellulose based materials surrounded by or located in the treated soil. Suitable soil-based control of termites is obtained by providing in the soil an effective dosage of a composition of this invention. For use in this manner, the active ingredient is suitably applied to the soil at a rate of from about 0.001 gram to about 10 kilograms per hectare. Depending on the composition used, good control of soil inhabiting termites is obtained at rates of from about 0.001 gram to about 1 kilogram per hectare and preferably from about 0.01 gram to 100 grams per hectare. The nepetalactone of this invention can conveniently be formulated for use as an extract-impregnated wooden stake, bait, granule or powder containing a solid diluent, or as a suspension concentrate. Such formulations generally comprise from about 0.01 to about 50% by weight of the active ingredient. Effective control results when the formulation is physically integrated into the topsoil, in a trench surrounding the vulnerable site, or when it is applied to the surface of the soil.

The compositions of this invention can also be applied as a drench, i.e., as a solution or dispersion of the compound in a suitable solvent or liquid diluent. Such drenches can be prepared by diluting with water a concentrate containing a nepetalactone of this invention, an emulsifying agent, and preferably an organic solvent, such as isophorone and/or N-methylpyrrolidone. The nepetalactone of this invention can be applied by band, furrow or side-dress techniques, and may be incorporated or not.

In another embodiment of the invention, the compositions of this invention are applied directly on or into the material to be protected or treated. For example, timber is treated either before, during or after its incorporation into a structure or building, thereby protecting it against damage from termite attack or combating an already existing infestation of termites. For treatment of timber, the composition can contain a penetrant designed to facilitate penetration of the active ingredient to a significant depth in the timber, thereby ensuring that superficial-surface abrasion will not generate a surface free from active ingredient and thus vulnerable to termite penetration.

Examples of materials known for use as wood penetrants include paraffinic hydrocarbons, for instance low aromatic white spirit, 2-ethoxyethanol and methyl isobutyl ketone. Preferably the penetrant is 2-ethoxyethanol or methyl isobutyl ketone, optionally in association with isophorone and/or N-methyl pyrrolidone. It is useful in such timber treatment to incorporate "anti-bloom" agent, which counteract the tendency for the active ingredient to migrate to the surface ("blooming"), suitable materials being dibutyl phthalate and o-dichlorobenzene.

Timber treatment compositions can also, if desired, contain fungicides (to prevent fungal attacks such as dry rot and wet rot), and/or pigments in order to combine termite protection with painting of the timber. In this context, painting will be understood to include not only the application of covering pigmentation (commonly white), but also the application of natural wood coloration in order to restore the appearance of weathered timber (e.g., as with treatments to red cedar external housing timbers).

The actual application onto or into the timber may be carried out using conventional techniques including immersion of the timber in the liquid, painting the liquid onto the timber by spray or brushing, and injecting the liquid into the timber.

The concentration of active ingredient in the treated timber should, of course, be sufficient to achieve the desired effect. However, the total volume of formulated product taken up by the timber is limited by the absorption properties of the wood with respect to that formulation and will also vary according to the application procedure adopted (immersing, painting or injecting); hence the concentration of active ingredient in the formulation should be such as to produce the desired concentration in the treated timber. The formulation may be aqueous, as for example obtained by dilution of a conventional insecticide emulsifiable concentrate, or non-aqueous such as an undiluted emulsifiable concentrate. The organic solvent in such formulations will suitably be one of those previously described.

Furthermore, according to another aspect of the invention, nepetalactone is added to and formulated for conventional paint or paints of various colors and qualities, for decorating and protecting, residential or commercial buildings, and other structures. Sealer materials for sealing floors, walls or driveways comprising nepetalactone to enhance anti-fungal properties are also invention embodiments. In another embodiment, the subject invention pertains to a conventional grout material having a nepetalactone as an additive. Preferably, the nepetalactone in the grout is encapsulated. Caulk material used to seal around sinks, baths, and showers may serve as a surface for fungal growth. Accordingly, another embodiment of the subject invention pertains to conventional caulk material comprising nepetalactone as an additive. Again, the nepetalactone may be provided in many different forms as described herein, but is typically provided in an encapsulated form. Other embodiments of the subject invention pertain to conventional cleaning solutions, whether they be designed for cleaning sinks, counter-tops, toilets, baths, showers, carpets, rugs, etc. Further still, another embodiment of the subject invention pertains to carpet or a rug whose fibers have been treated with nepetalactone to resist fungal growth. Similarly, another embodiment pertains to carpet padding treated with a nepetalactone composition. Yet another embodiment, pertains to carpet and/or rug sealers, such as Scotch-Guard type products containing nepetalactone.

The determination of the necessary parameters applicable to specific types of wood and particular treatment procedures can readily be determined by established techniques conventionally used by those skilled in the art.

All patents, patent applications and publications discussed or cited herein are understood to be incorporated by reference to the same extent as if each individual publication or patent application was specifically and individually set forth in its entirety.

Having generally described this invention, including the best mode thereof, those skilled in the art will appreciate that the present invention contemplates the embodiments of this invention as defined in the following claims, and equivalents thereof. However, those skilled in the art will appreciate that the scope of this invention should be measured by the claims appended hereto, and not merely by the specific embodiments exemplified herein. Those skilled in the art will also appreciate that more sophisticated technological advances will likely appear subsequent to the filing of this document with the Patent Office. To the extent that these later developed improvements embody the operative principles at the heart of the present disclosure, those improvements are likewise considered to come within the ambit of the following claims.

A broad range of organic molecules have been found to have fungicidal and bactericidal properties and are effectively used for plant disease control. However, many of the currently used pesticides pose a high risk to human health and the environment and are not biodegradable. Since the establishment of the Environmental Protection Act in 1972 there has been an increased concern over the use of toxic chemicals for plant disease control and the dangerous residual potential these toxic products represent. The United States Congress disclosed its concerns with those products with the passage of the Food Quality Protection Act in August, 1996 which requires the U.S. EPA to reassess each existing pesticide by 2006. Because of toxicity concerns, to reduce residues on crops, fruits and vegetables, the application of pesticides shortly before harvest must usually be avoided. Additionally, because of concerns regarding the health of workers, entry into fields or greenhouses shortly after pesticide application is usually prohibited.

Therefore, there is a real need to provide more biocompatible fungicides and bactericides which are, by definition, safe in the environment, non-toxic to humans and animals, and which are rapidly biodegradable.

What is claimed is:

1. A method of inhibiting or reducing algae growth, comprising contacting algae or algae susceptible structure, with an amount of a nepetalactone composition comprising an anti-algae effective concentration of nepetalactone.

2. The method of claim 1, wherein said structure is an exposed interior or exterior surface of an exterior wall of a building.

3. The method of claim 1, wherein said structure is a surface of a plumbing chase or interior wall surface of a wall that covers, at least partially, a plumbing chase.

4. The method of claim 1, wherein said structure is all or a portion of a building flooring, subflooring or decking.

5. The method of claim 1, wherein said structure is an exterior surface of a roof.

6. The method of claim 1, wherein said nepetalactone composition comprises a nepetalactone concentration of about 0.0001 to about 10 percent, by weight, of said composition.

7. The method of claim 1, wherein said nepetalactone composition comprises a nepetalactone concentration of about 0.005 to about 5 percent, by weight, of said composition.

8. The method of claim 1, wherein said nepetalactone composition comprises a nepetalactone concentration of about 0.01 to about 1 percent, by weight, of said composition.

9. The method of claim 1, wherein said nepetalactone composition comprises water at about 90 to about 99.99 percent, by weight, of said composition.

10. The method of claim 1, wherein said nepetalactone composition comprises alcohol in a concentration of about 1 to about 50 percent, by weight, of said composition.

11. Lumber treated with a composition comprising nepetalactone.

12. The lumber of claim 11, wherein said lumber has been soaked in said composition.

13. A method of reducing algae present on at least one external surface of at least one external wall or roof of a building comprising contacting said algae with a nepetalactone composition comprising an anti-algae effective concentration of nepetalactone.

14. The method of claim 13, wherein said nepetalactone composition does not harm said external surface if intentionally left onto treated area without rinsing.

* * * * *